United States Patent
Kobilka et al.

(10) Patent No.: US 10,211,402 B2
(45) Date of Patent: Feb. 19, 2019

(54) DIBROMO-DIIODO-DIPOLYCYCLIC COMPOUND AND ELECTRON ACCEPTOR MOLECULES DERIVED THEREFROM

(71) Applicant: International Business Machines Corporation, Armonk, NY (US)

(72) Inventors: Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

(*) Notice: Subject to any disclaimer, the term of this patent is extended or adjusted under 35 U.S.C. 154(b) by 126 days.

(21) Appl. No.: 15/151,754

(22) Filed: May 11, 2016

(65) Prior Publication Data

US 2017/0331044 A1 Nov. 16, 2017

(51) Int. Cl.
| | |
|---|---|
| *H01L 51/00* | (2006.01) |
| *C08G 73/06* | (2006.01) |
| *C08G 67/00* | (2006.01) |
| *C08G 75/32* | (2006.01) |
| *C07D 311/76* | (2006.01) |
| *C07D 217/24* | (2006.01) |
| *H01L 51/42* | (2006.01) |

(52) U.S. Cl.
CPC ........ *H01L 51/0036* (2013.01); *C07D 217/24* (2013.01); *C07D 311/76* (2013.01); *C08G 67/00* (2013.01); *C08G 73/0672* (2013.01); *C08G 73/0688* (2013.01); *C08G 75/32* (2013.01); *H01L 51/0035* (2013.01); *H01L 51/0043* (2013.01); *H01L 51/4253* (2013.01)

(58) Field of Classification Search
CPC ..................................................... C08G 61/12
See application file for complete search history.

(56) References Cited

U.S. PATENT DOCUMENTS

| | | |
|---|---|---|
| 7,655,809 B2 | 2/2010 | Fallis et al. |
| 9,017,573 B2 | 4/2015 | Risser et al. |
| 9,029,695 B2 | 5/2015 | Facchetti |
| 9,035,004 B2 | 5/2015 | Facchetti et al. |
| 2015/0114468 A1 | 4/2015 | Kim et al. |
| 2015/0171332 A1 | 6/2015 | Drees et al. |
| 2015/0344630 A1 | 12/2015 | Wang et al. |

FOREIGN PATENT DOCUMENTS

GB  1279372 A * 6/1972 .......... C07D 217/24

OTHER PUBLICATIONS

Yu et al. "The C—H Activation/1,3-Diyne Strategy: Highly Selective Direct Synthesis of Diverse Bisheterocycles by Rh III Catalysis" Angew. Chem. Int. Ed. Jul. 2014, 53, 9650-9654. (Year: 2014).*
Woods et al. "3,3'-Biscoumarins", Journal of Chemical and Engineering Data, 1970, vol. 15, No. 2, 355-356. (Year: 1970).*
Yao, et al., "Synthesis of Isocoumarins and α-Pyrones via Electrophilic Cyclization", DOI: 10.1021/jo034308v, Publication Date (Web): Jul. 2, 2003, Copyright © 2003 American Chemical Society, 5 pages.

* cited by examiner

*Primary Examiner* — Nicole M. Buie-Hatcher
(74) *Attorney, Agent, or Firm* — Isaac J. Gooshaw (57) ABSTRACT

The present specification provides a di-polycyclic compound, and a polymer chain consisting of alternating electron donor compounds and electron acceptor compounds, which include the di-polycyclic compound.

18 Claims, 5 Drawing Sheets

FIG. 6 even
DIBROMO-DIIODO-DIPOLYCYCLIC COMPOUND AND ELECTRON ACCEPTOR MOLECULES DERIVED THEREFROM

BACKGROUND OF THE INVENTION

The present invention relates generally to the field of production and modification of a dibromo-diiodo-dipolycyclic compound, and more particularly to the generation of organic electron acceptor molecules.

Advances have been made towards the realization of organic semiconductor technology in everyday applications. For example, some organic electronics, such as organic light emitting diodes (OLEDs), may be used as part of energy efficient lighting systems. Other organic electronics, such as organic photovoltaics (OPVs), may offer a practical path to achieve low-cost, renewable energy. Many organic electronics can be solution processed into large-area thin-films, and can be fabricated into lightweight and flexible devices.

SUMMARY

According to one embodiment, a compound is disclosed. The compound comprising a di-polycyclic compound of the formula:

wherein:

I) a) $M_1$, $M_2$, $M_3$, and $M_4$, comprise a first aromatic ring; b) $M_7$, $M_8$, $M_9$, and $M_{10}$ comprise a second aromatic ring, and c) $M_5$ and $M_6$ independently of each other denote a carbon with i) a pi bond to a first carbon atom, and ii) a single bond to a carbon of an aromatic ring;

II) $M_2$ and $M_9$, independently of each other, denote one or more atoms that comprise binding sites for $X_1$ and $X_4$ respectively, wherein both $X_1$ and $X_4$ are electron donor groups;

III) $X_2$ and $X_3$ independently of each other denote one or both of: a) different substituent groups that differ based on one or more of elemental composition, bonding, and arrangement of atoms, and b) denote at least one atom that is part of a cyclic-chain of atoms connecting $M_5$ and $M_6$;

IV) $Z_1$ and $Z_2$ independently of each other denote at least one atom in a ring structure; and V) $Y_1$ and $Y_2$ independently of each other denote either a) a single substituent group comprising at least one atom, or b) a pair substituent groups each comprising at least one atom.

According to one embodiment, the di-polycyclic compound has a biisoquinoline core structure.

According to another embodiment, the di-polycyclic compound has biisocoumarin core structure.

According to one embodiment, the di-polycyclic compound is an electron acceptor compound included in a polymer chain consisting of alternating electron acceptor compounds and electron donor compounds.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

DETAILED DESCRIPTION

In general, the present disclosure relates to modifiable electron acceptor scaffolds and processes for forming such modifiable electron acceptor scaffolds/molecules/compounds. The present disclosure also relates to the formation of various electron acceptor scaffolds by selective modification of such modifiable electron acceptor scaffolds. The present disclosure further relates to the formation of various organic electronics and materials that include such electron acceptor scaffolds. One embodiment of the present disclosure provides an electron acceptor scaffold that is unexpectedly modifiable/customizable such that the solubility and electronic characteristics of the resulting electron acceptor are modified/customized.

Some embodiments of the present invention recognize the challenge in achieving polymers and small molecules that are soluble enough in common organic solvents to render them solution processable, while still maintaining a desired degree of crystallinity in a synthesized polymer, which in turn facilitates charge separation and transport in that polymer. Some embodiments of the present invention provide affixing alkyl side chains to aromatic molecules that make up a polymer (or small molecule) backbone to adjust the degree of crystallinity of the polymer. Some embodiments of the present invention provide a customizable polymer that is tuned to change its potential solubility and energy levels by modification of a backbone structure of an electron acceptor compound, which in turn alters one or more overall properties of the resulting polymer that includes that electron acceptor compound. For example, inclusion of an electron donating substituent/group increases the amount of photons harvested and the generation of coulombically bound electron-hole pairs in a portion of a polymer-polymer compound that includes that modified electron acceptor.

Embodiments of the present invention recognize that many polymers that have been successfully used in organic photovoltaics (OPVs) are comprised of an alternating electron-rich (donor) and electron-deficient (acceptor) comonomers, called donor-acceptor (D-A) copolymers. Embodiments of the present invention recognize that it may be much easier, for synthetic reasons, to affix alkyl chains to the donor molecules. As such, the library of known donor molecules can be much more diverse than that of the acceptor molecules.

Embodiments of the present invention provide a modifiable acceptor scaffold that can be further modified with various alkyl side chains for improved solubility. Some embodiments of the present invention recognize the use of biisocoumarin, and derivatives thereof, as a modifiable acceptor scaffold that can be further modified with various alkyl side chains for improved solubility. Some embodiments of the present invention recognize the use of dibromo-diiodo-biisocoumarin, and derivatives thereof, as a modifiable acceptor scaffold that can be further modified with various substituent groups, for example, alkyl side chains, for improved solubility and electronic characteristics (i.e. photon absorption/electron promotion, crystallinity, and electron transport).

Some embodiments of the present invention provide synthesis of modifiable acceptor scaffolds that can be further modified with various alkyl side chains for improved solubility. Some embodiments of the present invention provide synthesis of a polymer that includes modified acceptor scaffolds that have been modified with various alkyl side chains for improved solubility. Some embodiments of the present invention provide modification of acceptor scaffolds to vary the crystallinity of polymers that include the modified acceptor scaffold.

Some embodiments of the present invention provide acceptor molecules that have either a biisocoumarin or biisoquinoline core structure and can be modified to possess a different functional backbone or different alkyl side chains. Some embodiments provide such modified acceptor molecules that are included in D-A copolymers or D-A small molecules for use in OPVs. Some embodiments provide organic electronics, such as OPVs, electroluminescence devices, field effect transistors and the like, that include one or more kinds of modified acceptor molecules as described herein above. Some such embodiments recognize that one or both of the crystallinity and the electronic characteristics of a resulting polymer can be tuned by inclusion of more than one type of modified acceptor molecules as described herein above.

Note that while various reaction schemes are provided herein, one skilled in the art recognizes that numerous alternative reaction schemes may be employed that are within the scope of the present invention. As such, the chemical reactions presented herein are to be seen as exemplary and not limiting in nature. In general, many various combination of reagents and reactions may be employed to produce the compounds described herein, and are thus within the scope of the present invention.

Referring now to FIGS. 1A-1D, an example of a series of chemical reactions are provided that constitute a method of manufacture for the formation of electron acceptor scaffold 110 and disclose one composition thereof, in accordance with one exemplary embodiment. In general, electron acceptor scaffold 110 is one of a small molecule, a monomer, or an oligomer that has a conjugated backbone/core structure, e.g., an arene backbone. In some embodiments, electron acceptor scaffold 110 includes one or more of double bonds, triple bonds, heterocyclic ring structures, and homocyclic ring structures, or combinations thereof. For example, electron acceptor scaffold 110, or its derivatives as described with reference to FIGS. 2 and 3, can include substituted, mono-, di-, tri-, or other multicyclic aromatic ring structures. Non-limiting examples of such ring structures include, for example: phenyl, naphthyl, tolyl, anthracenyl, phenanthrenyl, and pyridine structures, e.g., pyridyl, quinolinyl. In some embodiments, such ring structures are joined by one or more of aryl groups, bridged aryl groups, and fused aryl groups; as non-limiting examples, indolyl and thienyl. In general, electron acceptor scaffold 110 includes at least one substituent that generates a leaving group(s) during the process of polymerization between electron acceptor scaffold 110 and an electron donor polymer. Further, such leaving groups are included in the derivatives of electron acceptor scaffold 110 as is further described with reference to FIG. 2.

As such, electron acceptor scaffold 110 includes sites that provide for both polymerization of electron acceptor scaffold 110, and derivatives thereof, as well as for the customization of electron acceptor scaffold 110, and derivatives thereof, to achieve a given solubility and physical/electronic characteristics as described in further detail herein and as understood by one of ordinary skill in the art. In general, the modification of electron acceptor scaffold 110 to form customized electron acceptor compounds facilitates the use of electron acceptor scaffold 110 and those derivatives as part of solution processing of polymer-polymer compound production. For example, one or more hydrogen(s) of electron acceptor scaffold 110 is replaced with a hydrocarbon chain of a given length and branching such that the now modified electron acceptor scaffold 110 is more soluble in a given solvent. The now modified electron acceptor is used in a polymerization reaction along with a given electron donor compound to form a polymer (i.e. the polymer-polymer compound). In another example, one or more hydrogen of electron acceptor scaffold 110 is replaced with a halogen, thereby forming a site for either polymerization or additional modification of electron acceptor scaffold 110. In another example, a carbon in a carbon ring of electron acceptor scaffold 110 is replaced with nitrogen bound to a functional group, thereby imparting new physical/electronic characteristics to the now modified electron acceptor scaffold 110. In some embodiments, a decrease in solubility due to the addition of a halogen group is countered by the addition of a hydrocarbon to electron acceptor scaffold 110, such that the resulting modified electron acceptor scaffold 110 has a desired degree of solubility in a given solvent.

In general, electron acceptor scaffold 110 is modifiable such that numerous types of customized electron acceptor compounds can be formed from it, i.e., by modification of electron acceptor scaffold 110. In this embodiment and example, electron acceptor scaffold 110 is a polyhalogen-biisocoumarin, such as, for example, a dibromo-diiodo-biisocoumarin compound. For further details regarding such modifications of electron acceptor scaffold 110, refer to the description of FIG. 2.

Figure 1A:
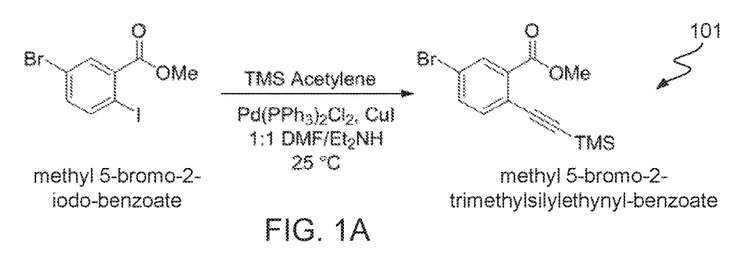
FIG. 1A-D is a chemical reaction diagram showing a series of chemical reactions that constitute a method of manufacture for the formation of an electron acceptor scaffold, in accordance with an exemplary embodiment of the present invention.

In FIG. 1A, a chemical reaction, 101, is provided for the formation of methyl 5-bromo-2-trimethylsilylethynyl-benzoate using methyl 5-bromo-2-iodo-benzoate as a starting material. In this reaction, Sonogashira cross-coupling of trimethylsilyl (TMS) acetylene is such that the iodine of methyl 5-bromo-2-iodo-benzoate is replaced with trimethylsilylethyne (TMS) acetylene. For example, in one embodiment, in chemical reaction 101, TMS acetylene is reacts with methyl 5-bromo-2-iodo-benzoate in the presence of a palladium catalyst, for example bis-(triphenylphosphine)-palladium(II) dichloride, denoted Pd(PPh$_3$)$_2$ in FIG. 1A, and a copper catalyst, such as copper iodide, denoted CuI in FIG. 1A, using a deoxygenated solvent or solvent mixture that includes an organic amine, for example 1:1 dimethylformamide (DMF)/diethylamine (Et$_2$NH) solvent solution, at 25° C. Upon completion, the solvent may be removed in vacuo, and the resulting slurry may be purified further by either standard aqueous workup conditions or filtration conditions. The crude product may be purified by recrystallization, column chromatography or by a variety of techniques known to those skilled in the art.

Figure 1B:
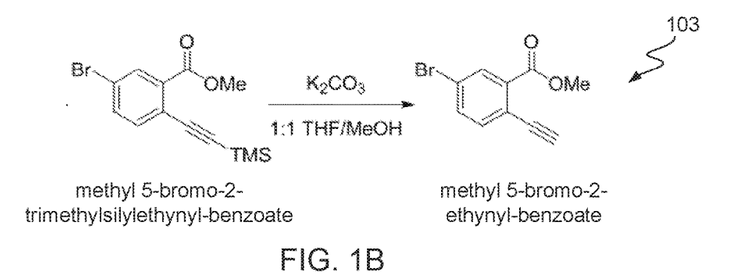

In FIG. 1B, a chemical reaction, 103, is provided for the formation of methyl 5-bromo-2-ethynyl-benzoate using methyl 5-bromo-2-trimethylsilylethynyl-benzoate as a starting material. For example, in one embodiment, in chemical reaction 103, the TMS group is removed by reaction of methyl 5-bromo-2-trimethylsilylethynyl-benzoate with potassium carbonate (K$_2$CO$_3$) using a 1:1 Tetrahydrofuran (THF)/methanol (MeOH) solvent solution. This cleavage of the trimethylsilylethynyl group from methyl 5-bromo-2-trimethylsilylethynyl-benzoate leaves ethyne as the terminal group. The reaction mixture is stirred until completion and most of the solvent may be removed in vacuo. The resulting slurry may be added to water and may be extracted with DCM (3 times). The combined organic layers may be combined and may be washed with brine and dried over magnesium sulfate (MgSO$_4$). This may be filtered and the solvents may be removed in vacuo. The crude product may be purified via column chromatography or by a variety of techniques known to those skilled in the art.

Figure 1C:
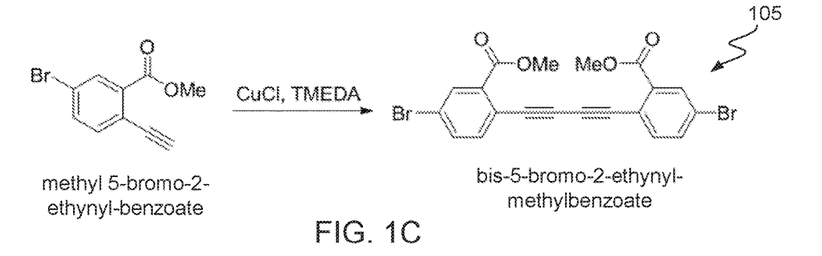

In FIG. 1C, a chemical reaction, 105, is provided for the formation of bis-5-bromo-2-ethynyl-methylbenzoate using methyl 5-bromo-2-ethynyl-benzoate as a starting material. In chemical reaction 105, Glaser-Hay homocoupling is utilized to form a diyne by formation of a bond between the terminal ethynyl groups of two methyl 5-bromo-2-ethynyl-benzoate molecules. For example, in one embodiment, in chemical reaction 105, the formation of a bond between two methyl 5-bromo-2-ethynyl-benzoate is catalyzed by the presence of a copper complex, such as a complex formed by tetramethylethylenediamine (TMEDA) and copper (I)-chloride (CuCl), which is, as is known to those skilled in the art, soluble in a range of solvents such as DMF, DCM, CHCl3, toluene, chlorobenzene, or THF, etc. The reaction mixture is stirred until completion and most of the solvent may be removed in vacuo. The resulting slurry may be added to water or aqueous ammonium hydroxide solution and may be extracted with DCM (3 times). The combined organic layers may be combined and may be washed with brine and dried over magnesium sulfate (MgSO$_4$). This may be filtered and the solvents may be removed in vacuo. The crude product may be purified via column chromatography or by a variety of techniques known to those skilled in the art.

Figure 1D:
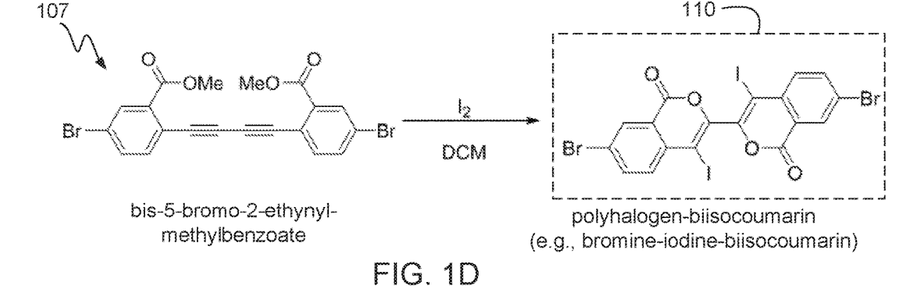

In FIG. 1D, a chemical reaction, 107, is provided for the formation of a bis-polycyclic ring system herein designated electron acceptor scaffold 110, which is, in this embodiment, a polyhalogen-biisocoumarin (e.g., bromine-iodine-biisocoumarin). For example, in one embodiment, chemical reaction 107 uses bis-5-bromo-2-ethynyl-methylbenzoate as a starting material to form electron acceptor scaffold 110. Note that in chemical reaction 107, formation of cyclic structures is facilitated by an iodine-promoted cyclization in a dichloromethane (DCM) solvent, leading to the formation of the polyhalogen-biisocoumarin, e.g., a bromine-iodine-biisocoumarin (DBDBC) molecule. This is accomplished by adding iodine or a solution of iodine in DCM, in excess, to a stirred solution of bis-5-bromo-2-ethynyl-methylbenzoate (the starting material), which may be at room temperature or cooled to −78° C. The reaction mixture may then be warmed to room temperature and stirred until completion. Any unreacted iodine may be quenched by an aqueous reagent such as sodium thiosulfate and the layers may be separated. The aqueous layer may be extracted with DCM (3 times). The combined organic layers may be combined and may be washed with brine and dried over magnesium sulfate (MgSO$_4$). This may be filtered and the solvents may be removed in vacuo. The crude product may be purified via column chromatography or by a variety of techniques known to those skilled in the art.

Figure 2:
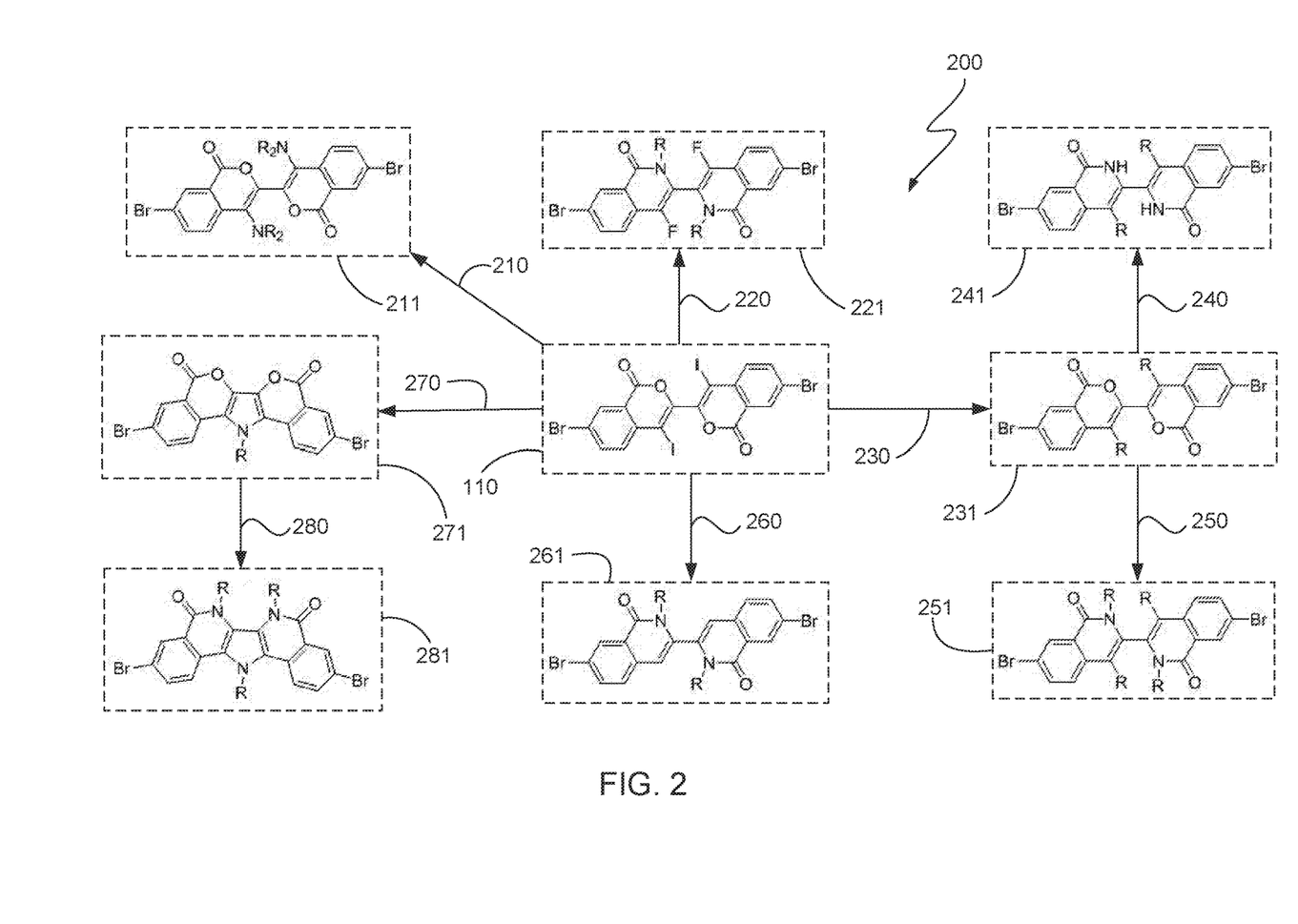
FIG. 2 is a chemical reaction diagram that illustrates examples of various chemical reactions that constitute one or more methods to generate various modified electron acceptor compounds and discloses their compositions, in accordance with an exemplary embodiment of the present invention.
Figure 3:
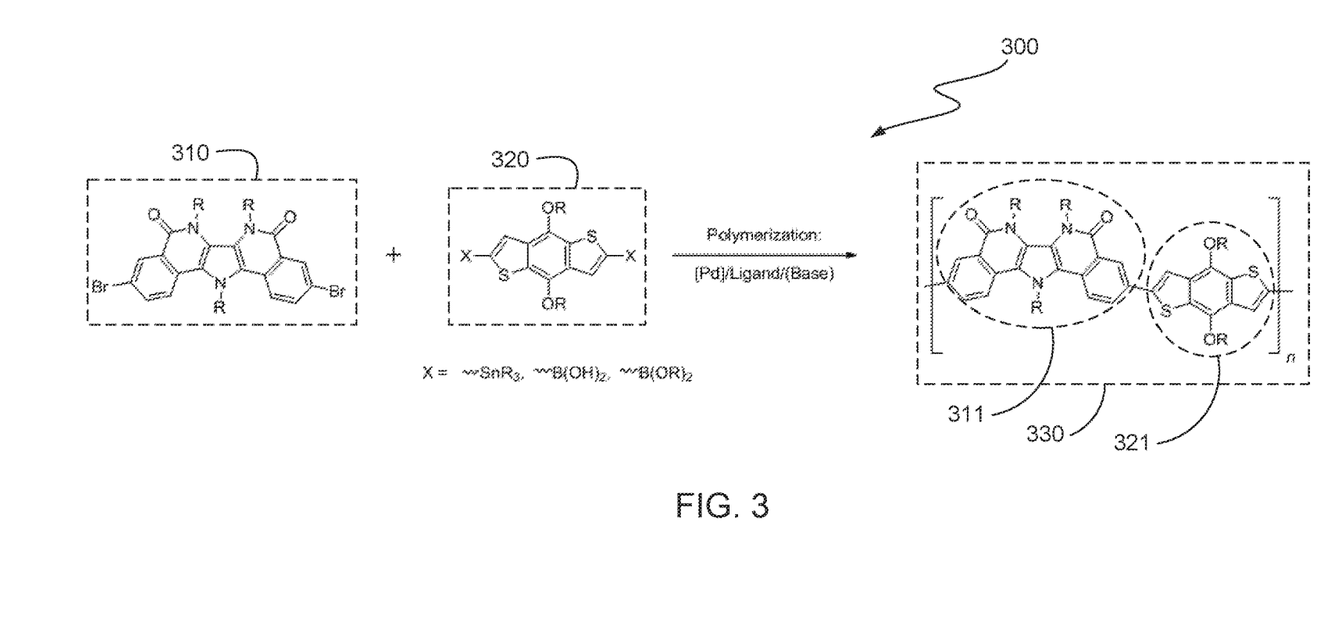
FIG. 3 illustrates a polymerization reaction, 300, that includes an electron acceptor compound, in accordance with an exemplary embodiment of the present invention.

It should be noted that the location of the bromine facilitates polymerization with electron-rich compounds (i.e. electron-donating molecules/monomers, electron-donor molecules, etc.), as shown in FIG. 3. Further note that the location of the iodine facilitates a wide variety of subsequent reactions for further customization of the electron acceptor scaffold 110, e.g., of a polyhalogen-biisocoumarin, as shown in FIG. 2. Note that in some embodiments, the versatility of the electron acceptor scaffold to form many customized, or customizable, electron acceptor compounds provides a variety of desirable traits relating to the manufacture of organic electronic devices. Some such traits may relate to performance characteristics, such as energy output and efficiency, and ease of use in the manufacture of certain organic electronic devices. For example, a given manufacturing technique requires that a given electron acceptor compound have a certain solubility in a solvent. Further, in some scenarios, a threshold of photon energy conversion is desired. As such, in some embodiments, a given electron acceptor compound is modified to include additional substituent groups and core structure(s) such that the resulting electron acceptor compound is predicted to achieve that threshold of photon energy conversion, i.e. is photoactive above a threshold.

In general, as used herein, substituent groups may include or be a chemical element selected from the group consisting of the following: fluorine, chlorine, bromine, iodine, arsenic, antimony, bismuth, silicon, tin, germanium, boron, carbon, oxygen, nitrogen, sulfur, and phosphorus. For example, one substituent group attached to a carbon of a homocyclic ring (i.e. a homocyclic structure) of electron acceptor scaffold is bromine and another substituent group attached to a carbon of a heterocyclic ring (i.e., a heterocyclic structure) of electron acceptor scaffold is iodine. As used herein, a homocyclic ring refers to a cyclic structure of atoms that constitute a single chemical element. For example, benzene is a homocyclic ring because only carbon constitutes the atoms included in the ring itself. As used herein, a heterocyclic compound or heterocyclic ring structure is a cyclic compound that has atoms of at least two different chemical elements as members of its ring(s). For example, pyridine, which has both carbon and nitrogen as members of its ring structure.

Referring now to FIG. 2, FIG. 2 illustrates examples of various chemical reactions that constitute one or more methods to generate various modified electron acceptor compounds and disclose their compositions, in accordance with certain exemplary embodiments. As shown in FIG. 2, these modified electron acceptor compounds are produced using electron acceptor scaffold 110 as starting material. In general, electron acceptor scaffold 110 is modified by one or more chemical reactions 210, 220, 230, 240, 250 260, 270, and 280. The result of this modification of electron acceptor scaffold 110 is the respective formation of one or more of electron acceptor compounds 211, 221, 231, 241, 251, 261, 271, and 281. It is to be noted that with each of the electron acceptor compounds 211, 221, 231, 241, 251, 261, 271, and 281 at least one substituent group (R) is denoted as being included. In this embodiment, such substituent groups provide additional customization for one or more of solubility and physical/electronic characteristics (i.e. photon absorption/electron promotion, crystallinity, and electron transport). General examples of such substituent groups include, but are not limited to, aryl, alkyl, and halogen groups.

In some embodiments, substituent groups, for example, the two such R groups, can be either the same as or different from each other. Further, each such substituent group can be independently selected from the group consisting of: hydrogen; deuterium; a halogen group; a nitrile group; a nitro group; an imide group; an amide group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group (i.e. an alkylthiol/thio group); a substituted or unsubstituted arylthioxy group (i.e. an arylthiol/thio group); a substituted or unsubstituted alkyl sulfoxide group; a substituted or unsubstituted aryl sulfoxide group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; and a substituted or unsubstituted heterocyclic ring group including one or more of nitrogen, oxygen, phosphorus, and sulfur atoms, or two adjacent substituents may be bonded to each other to form a hydrocarbon ring or a heterocyclic ring.

It should be further noted that some substituent groups constitute or include chemically active sites that are configured to provide for further modification of a polymer during or post polymerization. For example, a polymer is formed using an electron acceptor compound that has a substituent binding site, which is configured to bind a fullerene molecule after a polymerization process has completed to a threshold of fifty percent. In this example, as polymerization progresses, heat is applied to drive off excess solvent, which in turn increases the solubility of the fullerene until it is energetically favorable for the fullerene to bind to the binding site. In some such embodiments, not all such binding sites bind to fullerene. For example, if the electron acceptor compound/binding site is in excess relative to the fullerene, then only some of the substituent binding sites will bind a fullerene. As such, when the polymerization of a solution with that electron acceptor compound reaches fifty percent completion, a chemical reaction begins that binds fullerene molecules to the binding sites.

In some embodiments, an electron acceptor compound includes a variety of substituent groups, i.e. two or more different types of substituents. For example, an electron acceptor compound includes two substituent groups (R) at two different location on the electron acceptor compound, namely a propyl substituent group and a tert-butyl substituent group.

As described hereinafter with reference to the reactions denoted in FIG. 2, iodine, due to its nature and location on electron acceptor scaffold 110, comprises a leaving group that facilitates the modification of electron acceptor scaffold 110 through various reactions to generate customized electron acceptor compounds.

Referring now to chemical reaction 210 of FIG. 2, electron acceptor scaffold 110 is modified by chemical reaction 210. In chemical reaction 210, synthesis of electron acceptor compound 211 that has a biisocoumarin type of core structure, for example, a dialkylamino-biisocoumarin type of core structure, is disclosed. In this example, synthesis of electron acceptor compound 211 is achieved by substitution of dialkylamine groups for the iodine constituents of electron acceptor scaffold 110 under Hartwig-Buchwald cross-coupling conditions, e.g., via reaction of electron acceptor scaffold 110 with/under $HNR_2$, $Pd(dba)_2$, $P(o\text{-}Tol)_3$, $NaO^tBu$.

Referring now to chemical reaction 220 of FIG. 2, electron acceptor scaffold 110 is modified by chemical reaction 220. In chemical reaction 220, synthesis of electron acceptor compound 221 that has a biisoquinolinone type of core structure, for example, a difluoro-N-alkylated biisoquinolinone type of core structure, is disclosed. In this example, synthesis of electron acceptor compound 221 is achieved via an amination reaction using electron acceptor scaffold 110, followed by a copper catalyzed fluorination reaction, e.g., via reacting electron acceptor scaffold 110 with/under i) $H_2NR$, heat; followed by reactions with/under ii) [Cu], AgF.

Referring now to chemical reaction 230 of FIG. 2, electron acceptor scaffold 110 is modified by chemical reaction 230. In chemical reaction 230, synthesis of electron acceptor compound 231 that has a biisocoumarin core structure, for example, a dialkylamino-biisocoumarin, is disclosed. In this example, synthesis of electron acceptor compound 231 is achieved by Sonogashira cross-coupling reaction of electron acceptor scaffold 110 with an alkyne, followed by complete hydrogenation of the alkyne, e.g., via reaction of electron acceptor scaffold 110 with/under i) $Pd(PPh_3)_2Cl_2$, $NEt_3$, alkyne-R; followed by reaction with/under ii) $H_2$, Pd/C.

Referring now to chemical reaction 240 of FIG. 2, an electron acceptor compound, 241, is disclosed. As shown, electron acceptor compound 241 has, generally, a biisoquinolinone type of core structure. In this example, such a biisoquinolinone type of core structure is formed by modifying the biisocoumarin core structure of electron acceptor compound 231 using chemical reaction 240 to yield electron acceptor 241. Note that, more specifically, electron acceptor 241 has an alkylbiisoquinolinone type of core structure. In chemical reaction 240, synthesis of electron acceptor compound 241 is achieved by amidation from hydroxylamine (with acidic removal of the residual N-hydroxyl group), e.g., via reaction of electron acceptor compound 231 with/under i) $NH_2OH$, heat; followed by reaction with/under ii) $H_3O^+$.

Referring now to chemical reaction 250 of FIG. 2, an electron acceptor compound, 251, is disclosed. As shown, electron acceptor compound 251 has, generally, a biisoquinolinone type of core structure. In this example, such a biisoquinolinone type of core structure is formed by modifying the biisocoumarin core structure of electron acceptor compound 231 by chemical reaction 250 to yield electron acceptor 251. Note that, more specifically, electron acceptor 251 has an N-alkylated alkylbiisoquinolinone type of core structure. In chemical reaction 250, synthesis of electron acceptor compound 251 is achieved by amidation with an alkylamine, e.g., via reaction of electron acceptor compound 231 with/under $H_2NR$, heat.

Referring now to chemical reaction 260 of FIG. 2, electron acceptor scaffold 110 is modified by chemical reaction 260. In chemical reaction 260, synthesis of electron acceptor compound 261 that has a biisoquinolinone type of core structure, for example, an N-alkylated alkylbiisoquinolinone type of core structure, is disclosed. In this example, synthesis of electron acceptor compound 261 is achieved by applying an amidation reaction with an alkylamine, e.g., via reactions of electron acceptor scaffold 110 with/under i) fac-Ir(ppy), $HCO_2H$, $^nBu_3N$, flow reactor; and with/under ii) $H_2NR$, heat.

Referring now to chemical reaction 270 of FIG. 2, electron acceptor scaffold 110 is modified by chemical reaction 270. In chemical reaction 270, a synthesis of electron acceptor compound 271, which has a biisocoumarin type of core structure, is disclosed. Note that the biisocoumarin type of core structure of electron acceptor compound 271, in contrast to those of electron acceptor compound 211 and electron acceptor compound 231, includes a nitrogen that bridges the two respective isocoumarin portions, thereby forming a pyrrole structure in electron acceptor compound 271. More specifically, as shown, electron acceptor compound 271 is seen to have a pyrrolo-biiscoumarin type of core structure. In this example, synthesis of electron acceptor compound 271 is achieved by a Hartwig-Buchwald cross-coupling with a mono-alkylamine, e.g., via reaction of electron acceptor scaffold 110 with/under $H_2NR$, $Pd(dba)_2$, $P(o-Tol)_3$, $NaO^tBu$.

Referring now to chemical reaction 280 of FIG. 2, an electron acceptor compound with a biisocoumarin core structure is further modified by chemical reaction 280 to yield, in general, an electron acceptor with a biisoquinolinone type of core structure. For example, as disclosed, the core structure of electron acceptor compound 271 is modified to form an alkylated pyrrolo-alkylated isoquinolinone type of core structure. Note that the biisocoumarin type of core structure of electron acceptor compound 271 is converted to a biisoquinolinone type of core structure, but still retains the bridging nitrogen, which now bridges the two respective isocoumarin portions, thereby forming the pyrrole structure of electron acceptor compound 281. Even more specifically, in chemical reaction 280, electron acceptor compound 281 is shown to have an N-alkylated pyrrolo-bis-N-alkylated isoquinolinone type of core structure. In this example, synthesis of electron acceptor compound 281 is achieved by amidation reaction using an alkylamine, e.g., via reaction of electron acceptor compound 271 with/under $H_2NR$, heat.

While a select number of derived electron acceptor compounds have been presented herein, this selection is not to be interpreted as limiting. One skilled in the art recognizes that many other variations of such electron acceptor compounds are possible and are thus, within the scope of the current invention.

Referring now to FIG. 3, FIG. 3 illustrates a polymerization reaction, 300, that includes an electron acceptor compound, in accordance with one exemplary embodiment of the present invention. In polymerization reaction 300, an electron acceptor compound 310 is shown to form a bond with one or more electron donating compound 320. Note that electron acceptor compound 310, electron donating compound 320, and polymer 330 each includes multiple substituent groups (denoted by one or both of "X" and "R"). In the disclosed embodiment, in FIG. 3, each X substituent group is one of an $—SnR_3$ group, a $—B(OH)_2$ group, or a $—B(OR)_2$ group. Note that these substituents groups are non-limiting examples as other substituents groups are possible, as understood by one of ordinary skill in the art. The result of polymerization reaction 300 is the generation of polymer 330, which includes an electron acceptor portion, denoted using dashed circle 311, and an electron donor portion, denoted using dashed circle 321. In this example, as is shown in FIG. 3, polymerization reaction 300 is facilitated by the use of [Pd]/Ligand/(base). In some embodiments, polymerization reaction 300 is a Suzuki cross-coupling polymerization reaction that utilizes a boronic acid/ester monomer (e.g., where the X substituent group is one of a $—B(OH)_2$ group or a $—B(OR)_2$ group). Such embodiments also utilize a base, i.e. as indicated by "(base)" in FIG. 3, to facilitate the polymerization reaction. Further, in some such embodiments, the Suzuki cross-coupling polymerization reaction utilizes organic/aqueous two liquid phase conditions, and a phase transfer catalyst such as, for example, but is not limited to, tetrabutylammonium bromide or aliquat 336 (Starks' catalyst). In some embodiments, polymerization reaction 300 is a Stille cross coupling reaction that utilizes a trialkyltin compound (e.g., where the X substituent group is an $—SnR_3$ group). In some such embodiments, the inclusion of the base is not required. Note that in this example, electron acceptor compound 310 is represented as having the same structure as electron acceptor compound 281. However, this is for illustrative purposes only. One skilled in the art recognizes that many other combinations between such electron acceptor compounds and electron donor compounds are possible and are thus within the scope of the current invention.

Further one skilled in the art recognizes that many variations of polymers may be produced through the combinations of different types of electron donor compounds and different types of electron acceptor compounds. For example, in one embodiment a mixture of two different electron acceptor compounds are used to form a polymer that has desired characteristics. In some embodiments, such mixtures are configured to meet the requirements of a specific manufacturing environment. In general, such combinations of electron acceptor compounds and electron donor compounds are selected to produce a polymer under a set of reaction conditions. For example, monomers such as various electron acceptor compounds and electron donor compounds and their associated polymers (which are used in, as a non-limiting example, the production of electronics) are selected based on solubility. In some embodiments, electron acceptor compounds are modified to achieve a desired solubility for a specific production process. For example, electron donor A is highly soluble in solvent X. As such, electron acceptor compound Z is modified to include one or more substituent groups to improve the solubility of electron acceptor compound Z in solvent X. In this example, electron acceptor compound Z is modified such that its solubility in solvent X is within a threshold of electron donor A such that both can achieve similar molar ratios when in solution with solvent X.

Figure 4:
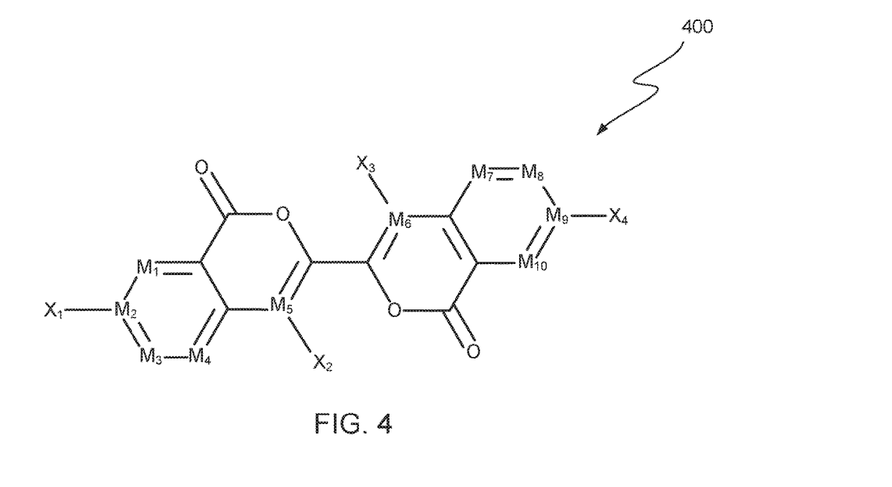
FIG. 4 illustrates a reference structure corresponding to an electron acceptor scaffold, in accordance with one exemplary embodiment of the present invention.

FIG. 4 illustrates a reference structure, 400, corresponding to an electron acceptor scaffold, in accordance with one exemplary embodiment of the present invention. In FIG. 4, select carbon atoms of the compound are designated using an "M" with a subscript. Further in FIG. 4, select substituents of the compound are designated using an "X" with a subscript. For example, if a direct correlation were made between the reference structure of FIG. 4 and the structure of electron acceptor scaffold 110 as shown in FIG. 1D, then $X_1$ and $X_4$ represent bromine substituents and $X_2$ and $X_3$ represent iodine substituents respectively bonded to carbon atoms designated $M_2$, $M_5$, $M_6$ and $M_9$. It should be noted that in various embodiments the substituents of $M_1$-$M_9$ can be different. For example, with reference to the structure of electron acceptor 271, $X_2$ and $X_3$ together represent a single nitrogen that forms a bridge between $M_5$ and $M_6$. Such differences may facilitate or otherwise impact solubility and potential electronic properties of the electron acceptor scaffold and derivatives thereof used for, as a non-limiting example, optoelectronics production. However, it is to be noted that the structure illustrated in FIG. 4 clearly shows a biisocoumarin core structure with at least three substituent groups being attached at select points thereon, of which at least two facilitate polymerization.

Figure 5:
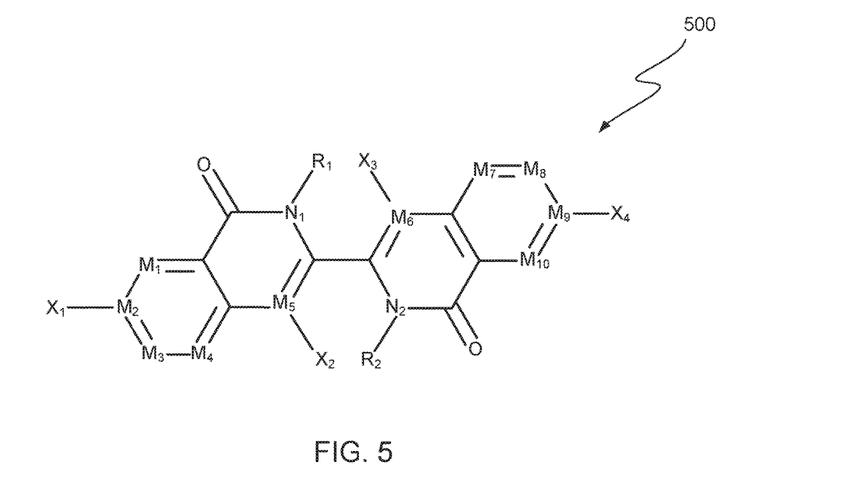
FIG. 5 illustrates a reference structure corresponding to an electron acceptor scaffold, in accordance with one exemplary embodiment of the present invention.

FIG. 5 illustrates a reference structure, 500, corresponding to an electron acceptor scaffold, in accordance with one exemplary embodiment of the present invention. In FIG. 5, select carbon atoms of the compound are designated using an "M" with a subscript. Further in FIG. 5, select substituents of the compound are designated using an "X" or "R" along with a subscript. For example, if a correlation were made between the reference structure of FIG. 5 and the structure of electron acceptor 241 as shown in FIG. 2, then $X_1$ and $X_4$ represent bromine substituents, $X_2$ and $X_3$ can represent alkyl substituents respectively bonded to carbon atoms designated $M_2$, $M_5$, $M_6$ and $M_9$. Further, reference structure 500 includes two nitrogen (designated $N_1$ and $N_2$) that respectively have a bound substituent group (designated $R_1$ and $R_2$). In electron acceptor 241 $R_1$ and $R_2$ correspond to hydrogen. It should be noted that in various embodiments the substituents of $M_1$-$M_9$, $N_1$ and $N_2$ can be different. For example, with reference to the structure of electron acceptor 281, $X_2$ and $X_3$ together represent a single nitrogen that forms a bridge between $M_5$ and $M_6$. Such differences may facilitate or otherwise impact the solubility of the electron acceptor scaffold and derivatives thereof during the production of various electronic products. However, it is to be noted that the reference structure illustrated in FIG. 5 clearly represents a biisoquinolinone core structure with at least three substituent groups being attached at select points thereon, of which at least two facilitate polymerization.

Figure 6:
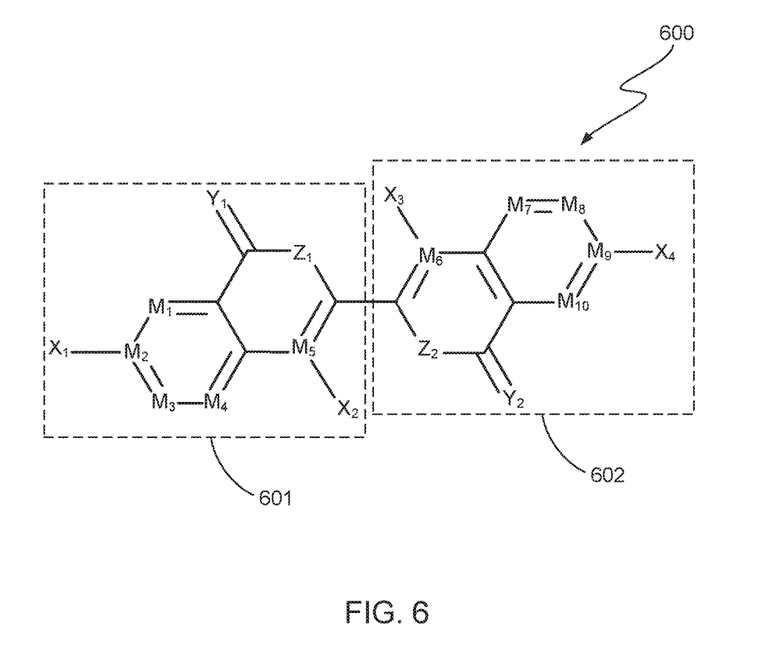
FIG. 6 illustrates a reference structure corresponding to an electron acceptor scaffold, in accordance with one exemplary embodiment of the present invention.

FIG. 6 illustrates a reference structure, 600, corresponding to an electron acceptor scaffold, in accordance with one exemplary embodiment of the present invention. In FIG. 6, select carbon atoms of the compound are designated using an "M" with a subscript. Further in FIG. 6, select substituents of the compound are designated using a "Y" with a subscript. An example of a substituent represented by one or both of $Y_1$ and $Y_2$ is an oxygen bound to a respective carbon of reference structure 600. In other embodiments, one or both of $Y_1$ and $Y_2$ represent two or more substituents bound to a carbon atom of reference structure 600. Further in FIG. 6, select substituents of the compound are designated using an "X" with a subscript. For example, if a direct correlation were made between the reference structure of FIG. 4 and the structure of electron acceptor scaffold 110 as shown in FIG. 1D, then $X_1$ and $X_4$ represent bromine substituents and $X_2$ and $X_3$ represent iodine substituents respectively bonded to carbon atoms designated $M_2$, $M_5$, $M_6$ and $M_9$. It should be noted that in various embodiments the substituents of $M_1$-$M_9$ can be different. Further, in reference structure 600, and in contrast to reference structure 400 and reference structure 500, the ring structures illustrated are not shown as containing either nitrogen or oxygen. Instead, reference structure 600 includes other elements designated using a "Z" with a subscript. For example, $Z_1$ and $Z_2$ can respectively be Sulphur, Carbon, or Phosphorus. In another example, $Z_1$ and $Z_2$ can respectively be one of a metal, metalloid, or a non-metal element, or a group thereof. In some embodiments, one or more substituents groups are bound to $Z_1$ and $Z_2$. In various embodiments, a given substituent of reference structure 600 can respectively be one of a metal, metalloid, or a non-metal element, or a group thereof, as would be appreciated by one of ordinary skill in the art. One of ordinary skill in the art further recognizes that one or more atom(s) of a given element, included in a ring structure, can be replaced with another atom of a different type of element. One example is the replacement of the ring bound oxygen of electron acceptor 271 with a ring bound nitrogen as shown in electron acceptor 281. Other like replacements can be made without deviation from the spirit and scope of the present invention. In some such embodiments, a variety of substituent groups may be bound to the elements represented by $Z_1$ and $Z_2$. Such differences may facilitate or otherwise impact solubility of the electron acceptor scaffold and derivatives thereof. It should also be noted that in various embodiments, substituents of $M_5$, $M_6$, $Z_1$, and $Z_2$ can form one or more ring structures therebetween. For example, with reference to the structure of electron acceptor 281, $X_2$ and $X_3$ together represent a single nitrogen that forms a bridge between $M_5$ and $M_6$. As such, ring structures connecting various combinations of $M_5$, $M_6$, $Z_1$, and $Z_2$ are within the spirit and scope of the present invention. For example, in one embodiment, $M_5$ and $M_6$ are joined together by one or more atoms to form a first ring structure, and $Z_1$ and $Z_2$ are joined together by one or more atoms to form a second ring structure. However, it is to be noted that the structure illustrated in FIG. 6 clearly shows a core structure that is substantially similar to both biisocoumarin core structure of FIG. 4 and the biisoquinolinone core structure of FIG. 5, with i) two polycyclic portions (indicated by dashed boxes 601 and 602) and ii) at least three substituent groups being attached at select points thereon, of which at least two facilitate polymerization. Note that in some embodiments, one or more ring structures may include portions of one or both of the illustrated polycyclic portions 601 and 602 such that the polycyclic portions 601 and 602 are one or both of i) joined into a single polycyclic structure and ii) include more cyclic structures attached to portions of one or both of the illustrated polycyclic portions 601 and 602.

In some embodiments, a given electron acceptor compound is modified post polymerization to further modify the electronic characteristics (i.e. photon absorption/electron promotion, crystallinity, and electron transport) of the polymer. In some such embodiments, additional substituent groups are added to or removed from an electron acceptor portion of a polymer, denoted using dashed circle 311 in FIG. 3. In some embodiments, an electron donor portion of a polymer, denoted using dashed circle 321 in FIG. 3, is also modified by addition or removal of substituent groups. In some such embodiments, modification of an electron acceptor portion of a polymer dictates, at least in part, the type or quantity of change that is applied to the electron donor portion of the polymer. One skilled in the art recognizes that various reactions may be carried out during or post polymerization without deviation from the scope and spirit of this disclosure.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular "herein" includes the plural (and vice versa) unless specifically stated otherwise. It should be understood that the order of steps or order for performing certain actions is immaterial so long as the present teachings remain operable. Moreover, two or more steps or actions may be conducted simultaneously.

As used herein, a component (such as a thin film layer) can be considered "photoactive" if it contains one or more compounds that can absorb photons to produce excitons for the generation of a photocurrent. In some scenarios, fill factor (FF) is the ratio (given as a percentage) of the actual maximum obtainable power, ($P_m$ or $V_{mp}*J_{mp}$), to the theoretical (not actually obtainable) power, ($J_{sc}*V_{oc}$). Accordingly, FF can be determined using the equation:

$$FF=(V_{mp}*J_{mp})/(J_{sc}*V_{oc})$$

where $J_{mp}$ and $V_{mp}$ represent the current density and voltage at the maximum power point ($P_m$), respectively, this point being obtained by varying the resistance in the circuit until J*V is at its greatest value; and $J_{sc}$ and $V_{oc}$ represent the short circuit current and the open circuit voltage, respectively. Fill factor is one parameter used in evaluating the performance of solar cells. Some commercial solar cells have a fill factor of 0.60% or greater.

As used herein, the open-circuit voltage ($V_{oc}$) is the difference in the electrical potentials between the anode and the cathode of a device when there is no external load connected. As used herein, the power conversion efficiency (PCE) of a solar cell is the percentage of power converted from incident light to electrical energy. The PCE of a solar cell can be calculated by dividing the maximum power point ($P_m$) by the input light irradiance (E, in W/m$^2$) under standard test conditions (STC) and the surface area of the solar cell (A, in m$^2$). STC typically refers to a temperature of 25° C., and an irradiance of 1000 W/m$^2$ with an air mass 1.5 (AM 1.5) spectrum.

As used herein, a "polymeric compound" (or "polymer") refers to a molecule including a plurality of one or more repeating units connected by covalent chemical bonds. The polymeric compound can have only one type of repeating unit as well as two or more types of different repeating units. When a polymeric compound has only one type of repeating unit, it can be referred to as a homopolymer. When a polymeric compound has two or more types of different repeating units, one or more of the terms heteropolymer, copolymer, or copolymeric compound can be used instead. For example, a formula for a copolymeric compound can include repeating units $M^a$ and $M^b$, where $M^a$ and $M^b$ represent two different repeating units. In some embodiments, the assembly of the repeating units in the copolymer can be head-to-tail, head-to-head, or tail-to-tail. In addition, in some embodiments, the copolymer can be a random copolymer, an alternating copolymer, or a block copolymer. For example, the repeating units $M^a$ and $M^b$ include a subscript to denote their respective mole fraction, i.e. $M^a_x$ and $M^b_y$. As such, some embodiments disclose a copolymer of $M^a$ and $M^b$ having x mole fraction of $M^a$ and y mole fraction of $M^b$ in the copolymer, where the manner in which comonomers $M^a$ and $M^b$ is repeated can be alternating, random, regiorandom, regioregular, or in blocks. In addition to its composition, a polymeric compound can be further characterized by its degree of polymerization (n) and molar mass (e.g., number average molecular weight ($M_e$) and/or weight average molecular weight ($M_w$) depending on the measuring technique(s)).

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, "halo" or "halogen" refers to fluoro, chloro, bromo, and iodo substituents. As used herein, "oxo" refers to a double-bonded oxygen (i.e., =O). As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neo-pentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, ten-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula —$C_sH_{2s+1-t}X^0_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxy, hexoxy groups, and the like. The alkyl group in the —O-alkyl group can be substituted as described herein.

As used herein, "alkylthio" refers to an —S-alkyl group. Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and optionally can be substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which optionally can be substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which optionally can be substituted as described herein.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, but is not limited to, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl(bicyclic), 2-naphthyl(bicyclic), anthracenyl(tricyclic), phenanthrenyl(tricyclic), pentacenyl(pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., $—C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an alkylaryl group, where the arylalkyl group is covalently linked to the defined chemical structure via the alkyl group. An arylalkyl group is within the definition of a $—Y—C_{6-14}$ aryl group, where Y is as defined herein. An example of an arylalkyl group is a benzyl group (—CH$_2$—C$_6$H$_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent C$_{1-20}$ alkyl group (e.g., a methylene group), a divalent C$_{2-20}$ alkenyl group (e.g., a vinylyl group), a divalent C$_{2-20}$ alkynyl group (e.g., an ethynylyl group), a divalent C$_{6-14}$ aryl group (e.g., a phenylyl group), a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

As is understood by one of ordinary skill in the art, the electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing.

At various places in the present specification, substituents may be disclosed in groups or in ranges. It is specifically intended that the description include each and every individual subcombination of the members of any such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and geometric isomers (diastereomers). The present teachings include such optical and geometric isomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one regioisomer includes any other regioisomers and any regioisomeric mixtures.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide (N$_3$), thiocyanate (SCN), nitro (NO$_2$), cyanate (CN), water (H$_2$O), ammonia (NH$_3$), and sulfonate groups (e.g., OSO$_2$—R, wherein R can be a C$_{1-10}$ alkyl group or a C$_{6-14}$ aryl group each optionally substituted with 1-4 groups independently selected from a C$_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

The present teachings relate to polymer-polymer blend semiconductor materials that include an electron-donor polymer and an electron-acceptor polymer, where the polymer-polymer blend semiconductor materials can provide unexpectedly high power conversion efficiencies (PCEs) when used as the photoactive layer in optoelectronic devices such as OPV cells. More specifically, both the electron-acceptor polymer and the electron-donor polymer can be described as π-conjugated polymers, where repeat units in the polymer backbone are made up of atoms with sp$^2$ and π covalent bonds resulting in alternating double and single bonds along the polymer backbone. The electron-acceptor polymer and the electron-donor polymer have different electron affinities and optical energy gaps. Specifically, the electron-donor polymer has a lower electron affinity (or lower ionization energy) than the electron-acceptor polymer and therefore functions as a p-type (hole-transporting) conduction area in the blend. Conversely, the electron-acceptor polymer has a higher electron affinity (or higher ionization energy) than the electron-donor polymer and therefore functions as an n-type (electron-transporting) conduction area in the blend. In addition, the electron-acceptor polymer can be characterized by both a lower $E_{HOMO}$ (highest occupied molecular orbital energy level) and a lower $E_{LUMO}$ (lowest unoccupied molecular orbital energy) that those of the electron-donor polymer. In some embodiments, the $E_{HOMO}$ of the electron-acceptor polymer can be lower than the $E_{HOMO}$ of the electron-donor polymer, while the $E_{LUMO}$ of the electron-acceptor polymer can be lower than the $E_{LUMO}$ of the electron-donor polymer.

Throughout the specification, structures may or may not be presented with chemical names. Where any question arises as to nomenclature, the structure prevails.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein, but is to be accorded the widest scope possible consistent with the principles and features as defined by the following claims.

What is claimed is:
1. A compound comprising:
   a polymer chain consisting of alternating electron acceptor groups and electron donor groups in which the electron acceptor groups include a di-polycyclic group of the formula:

wherein
   I)
      a) $M_1$, $M_2$, $M_3$, and $M_4$, comprise a first aromatic ring,
      b) $M_7$, $M_8$, $M_9$, and $M_{10}$ comprise a second aromatic ring, and
      c) $M_5$ and $M_6$ independently of each other denote a carbon with i) a pi bond to a first carbon atom, and ii) a single bond to a carbon of an aromatic ring;
   II) $M_2$ and $M_9$, independently of each other, denote one or more atoms that comprise binding sites for $X_1$ and $X_4$ respectively, wherein both $X_1$ and $X_4$ are electron donor groups;
   III) $X_2$ and $X_3$ independently of each other denote one or both of:
      a) different substituent groups that differ based on one or more of elemental composition, bonding, and arrangement of atoms, and
      b) denote at least one atom that is part of a cyclic-chain of atoms connecting $M_5$ and $M_6$;
   IV) $Z_1$ and $Z_2$ independently of each other denote at least one atom in a ring structure; and
   V) $Y_1$ and $Y_2$ independently of each other denote either
      a) a single substituent group comprising at least one atom, or b) a pair substituent groups each comprising at least one atom.

2. The compound of claim 1, wherein the at least one atom of one or both of $Z_1$ and $Z_2$ has at least one substituent group bound to it that includes at least one chemical element selected from the group consisting of: fluorine, chlorine, bromine, iodine, arsenic, antimony, bismuth, silicon, tin, germanium, boron, carbon, oxygen, nitrogen, sulfur, and phosphorus.

3. The compound of claim 1, wherein the at least one atom of one or both of $Z_1$ and $Z_2$ independently of each other denote a chemical element selected from the group consisting of: arsenic, antimony, bismuth, silicon, tin, germanium, boron, carbon, oxygen, nitrogen, sulfur, and phosphorus.

4. The compound of claim 1, wherein the at least one atom of one or both of $X_2$ and $X_3$ independently of each other denote a chemical element selected from the group consisting of: fluorine, chlorine, bromine, iodine, arsenic, antimony, bismuth, silicon, tin, germanium, boron, carbon, oxygen, nitrogen, sulfur, and phosphorus.

5. The compound of claim 1, wherein one or more of $M_1$, $M_3$, $M_4$, $M_7$, $M_8$, and $M_{10}$ independently of each other denote a carbon atom bound to one or both of i) a constituent that includes at least one chemical element selected from the group consisting of: fluorine, chlorine, bromine, iodine, arsenic, antimony, bismuth, silicon, tin, germanium, boron, carbon, oxygen, nitrogen, sulfur, and phosphorus, and ii) an electron donor group.

6. The compound of claim 1, wherein $X_1$ includes at least one chemical element bound to a carbon of the first aromatic ring, the chemical element selected from the group consisting of: arsenic, antimony, bismuth, silicon, tin, germanium, boron, carbon, oxygen, nitrogen, sulfur, and phosphorus.

7. The compound of claim 1, wherein $X_1$ denotes at least one chemical element that is included as part of a given electron donor group bound to $M_2$.

8. The compound of claim 1, wherein $X_4$ includes at least one chemical element bound to a carbon of the first aromatic ring, the chemical element selected from the group consisting of: arsenic, antimony, bismuth, silicon, tin, germanium, boron, carbon, oxygen, nitrogen, sulfur, and phosphorus.

9. The compound of claim 1, wherein $X_4$ denotes at least one chemical element that is included as part of a given electron donor group bound to $M_9$.

10. The compound of claim 1, wherein the at least one atom of one or both of $Z_1$ and $Z_2$ is either nitrogen or oxygen.

11. The compound of claim 1, wherein the at least one atom of both of $Y_1$ and $Y_2$ is oxygen.

12. The compound of claim 1, wherein the at least one atom of both of $X_2$ and $X_3$ is iodine.

13. The compound of claim 1, wherein the at least one atom of $X_3$ is nitrogen that forms a ring structure that includes $M_5$ and $M_6$.

14. The compound of claim 1, wherein the at least one atom of $X_2$ is nitrogen that forms a ring structure that includes $M_6$ and $M_5$.

15. The compound of claim 1, wherein the di-polycyclic group has a biisoquinoline core structure.

16. The compound of claim 15, wherein the di-polycyclic group has one or both of i) a cyclic structure that includes $M_5$, $X_2$ and $M_6$ and ii) a cyclic structure that includes $M_6$, $X_3$ and $M_5$.

17. The compound of claim 1, wherein the di-polycyclic group has biisocoumarin core structure.

18. The compound of claim 17, wherein the di-polycyclic group has one or both of i) a cyclic structure that includes $M_5$, $X_2$ and $M_6$ and ii) a cyclic structure that includes $M_6$, $X_3$ and $M_5$.

* * * * *